United States Patent [19]

Helentjaris et al.

[11] Patent Number: 5,324,631
[45] Date of Patent: Jun. 28, 1994

[54] METHOD AND DEVICE FOR IMPROVED RESTRICTION FRAGMENT LENGTH POLYMORPHISM ANALYSIS

[76] Inventors: Timothy Helentjaris, 7405 N. Stagecoach Dr., Park City, Utah 84124; Donna Shattuck-Eidens, 1936 Berkeley St., Salt Lake City, Utah 84108

[21] Appl. No.: 752,907

[22] Filed: Aug. 26, 1991

Related U.S. Application Data

[63] Continuation of Ser. No. 266,970, Nov. 3, 1988, abandoned, which is a continuation-in-part of Ser. No. 120,309, Nov. 13, 1987, abandoned.

[51] Int. Cl.$^5$ .................... C12Q 1/68; C12P 19/34; C07H 21/04; C12N 15/00
[52] U.S. Cl. ........................ 435/6; 435/91.2; 536/24.33; 935/77; 935/78
[58] Field of Search ............ 435/6, 91.2; 536/27; 935/77, 78

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,729,947 | 3/1988 | Midderdorf et al. | 435/6 |
| 4,795,699 | 1/1989 | Tabor et al. | 435/5 |
| 4,965,188 | 10/1990 | Mullis et al. | 435/6 |

OTHER PUBLICATIONS

Hopman et al., Histochemistry, (1986), 85:1–4.

*Primary Examiner*—Mindy B. Fleisher

[57] ABSTRACT

Improvements in the efficiency and sensitivity of restriction fragment length polymorphism (RFLP) detection in target sequences are realized by developing primers that are specific for nucleic acid sequences, labelling those primers with distinguishable, non-radioactive labels, such as chromophores, and applying the primers in sets such that, after amplification of the target sequence, specific sequences, in particular those of RFLPs, can be identified by virtue of the probe(s) which hybridized.

9 Claims, 10 Drawing Sheets

FIG. 2

```
                                                     238B
                                             ┌─────────────────┐
        10         20         30         40         50         60
CTGGAGCTGC AGCCGCCAGC GAAGAGCAGA GCGTCACGGG GGGTGGCAGA GGAAGAGGCG

238A--><--238AR
                                         ┌─────────────────────
        70         80         90        100        110        120
CCTGGAGCAA CGGACAGGTG GTGTCTCCAA AGGCTGAGCT GGACACGGCG GGGGAGAGAG

┐
       130        140        150        160        170        180
AGCATGGCAG TCCACTCCGG CAGAGATTTC CTCTCACAGG CGCACACACA CACTATCGCT 190        200        210        220        230        240
CTCTTTAGTC TTTACTCTTT ACGTTGGCAG CGAAAACAAA TACAAAAGCA GGAGATTGTG 250        260        270        280        290        300
TGATCGTTCT CTGCTTTCTT GGGATTAGAT TCTCTTCTTT TCTTAACACC TCTGCTGCTT

238AOL1
   ┌───────────────────┐
       310        320        330        340        350        360
TAGCAGGTTT CAATGAGTAT TAGTATTGTA GCGAACCCTT TTTTTGTTGC TTTGACGCGG 370        380        390        400        410        420
ACGACGTCNG CCCTTTGCAT TGCCCCGCCC CCAATGCATG CCCAGGAAAC AGCACTGCAA 430        440        450        460        470        480
TGATTTAGTG CTTGTTTTTT TTTACTGATG AATGATGATA GGACAGCGAG TTCTGATTCC 490        500        510        520        530        540
TGGGTGCTAG ACTGCTAGTA GAAAAAAAAC GTTTGGACCG ACACGGCGTG ATCATTACTT
```

FIG. 3

```
       550         560         570         580        590         600
TTTCCTCGGC  TGTATGATGA  GGCGACGACG  AGCATCCATT CCATGGCTTT  GGCTTGTGTT

238COL1
       610         620         630        640         650        660
TTTCCTCATC  TTTTTCTTCG  TACGCTCCGA  CTGTTCCGCT TCCTTGGCCG  GGCGCTCTTT 670         680         690        700         710        720
AAGTCTTTTA  CACTACATCA  GGAGCTGGGG  CTGTCCTCGC GCTTTGCCGA  AAGCGAAGAG 730         740         750        760         770        780
ACCGAAAGCG  TGCCTGCCGC  CCGTATTCAC  GCCGTGGGAG GGAGGGATGC  AGGATGCAAT 790         800         810        820         830        840
GCAAGGGAGA  AGGAGAAGGC  CTCTTCACTC  TGCCTTGCCT TGCCTTGCCG  CACCACCAGT

238C1
       850         860         870        880         890        900
CCACCACAGA  ATGCAATGCA  CTCTTGCACT  GCACTGATGA AATGTCTGAG  CCGAGCGAGC

GGACTGCAG
```

FIG. 4

```
          10         20         30         40         50         60
   CTGCAGCGGG AACTCGTAGC CGGCGTCGCA CACCATCTCC CAGCTCTGCA TCACCATCTC 288A
          70    ┌────  80         90 ────┐  100        110        120
   GTACCCGGAG ATCCTCCCCG CCGACGGTGC ACCACGTAGA CGTGTCGCCC CTGGCCCAGA 130        140        150        160        170        180
   CCCGGCGCAT CGCCGAGGTC GCCGTCCTTG AACGCGGCGT AGAACCGCCG TTCGCCGCCA 190        200        210        220        230        240
   GCACCGGCCC GGCCGTCCTC CTGGAGCACG CGCACGTCGT CCCGGAGCGC CGGCGCGGCT

288BOL1
   ┌──────          ──────┐
          250        260        270        280        290        300
   AGTCCTCCTC CTCGATCGCG GTTTCGAGCT CGCGCCGCTA GGAGTCCTCG TCGGGCCGCC 310        320        330        340        350        360
   GCTGCCGGTT GCGCTCTCCT CCGTCTCGGA CGCCCCTCGG CTTANCCGCT CTTCACGTGA 370        380        390        400        410        420
   GCGGTTGTGA GCCTTGTGGT GCCTCGGTGT CGGTGCCGAC AGGTGCTTGC CGTTCGGAGC 430        440        450        460        470        480
   CCTGGACTGC TGGACAGGAC GCAGAGGAGA TGTTACAGAA TTTATTATCA GCACGTTACC

288BOL2
                      ┌──────          ──────┐
          490        500        510        520        530        540
   AATGGCATCA CACATTTCCA GAGGAAAAGG ATCGATGCAA AGCAACAAGA TTTTTTCTGA
```

FIG. 5

```
           550         560         570         580         590         600
      AACCGGTGAA  TGGAGTGCGC  ATACCTACTA  GATTGAACTA  CTGCACCTGC  ACTGATGAAG 610         620         630         640         650         660
      ACAGAAGAGA  GGAAGAGGAG  AAATGGGAAA  ATCTGTTTTG  ATTCAGATAA  TCTTCTCAGG 670         680         690         700         710         720
      CCATCAAATA  ATAAGACTAA  GAGAAAATTG  TATGTATGTA  TGTCATTGTA  ATTTTGTCTA

288EOL2
           730         740       ┌  750         760  ┐ 770         780
      ATAACTTATT  TTGTCATTGT  AAATATACTA  AGCCCTTCTG  TGCCATCCGG  ATGCAATTTA 790         800         810         820         830         840
      TTATCTTTTT  ATGTTGTCGC  CAGTGACATA  GAAGNATTAA  AAAATTGTAT  GTTCTAATCT 850         860         870         880         890         900
      GTTCTAAGAA  ATTAGATCCA  AGTGGCATAA  AAGGGNATAA  AACATTTGCT  ATGATAAATA 910         920         930         940         950         960
      AGATATGAGA  CTAAATTACA  GTGANATAAA  GAGTAAGAGA  ATTATATACC  CTAATCCTTC

288EOL1
           970         980         990        1000      ┌ 1010        1020
      TATGCCACTA  ACGATAACAT  GAAAAAGCAT  CCGAGTGGGG  ATCATGACGT  TCGCGATACA 1030        1040        1050        1060        1070        1080
      AATAAGATAC  CAAACAAAAT  TCCAGTGACA  TATAGGGAAT  TGGCCCCAAG  AGTAAAGCTA
```

FIG. 6

```
          1090       1100       1110       1120       1130       1140
     AACGTCGTTA GGAGGATCAA GGCTAGAGCA GAGGTTACAT TATTCACTGC AAATTTTGTA 1150       1160       1170       1180       1190       1200
     AAAAAGAAGA AGACATAGAC ATCTTCTGTT GGTTTGCATA AACTACTAGC GTGTCTCTGA 288B, 288AR
          1210      ┌1220       1230      ┐1240       1250       1260
     TGCTGCATTT CCTTATTGTG ATGATGTCAC TTGGGGAAGA ACTCAAACCC TTAACGACAA 1270       1280       1290       1300       1310       1320
     GCTTAAGTGA AGAGGCACAC ATCAAATTAA GCCGAAGATC TGCCCCTAGA CTCCTACTGC
```

FIG. 7

```
           10         20         30         40         50         60
     CTGCAGAACC TCCTCTCTTT ATCAGGCTAT GTCAAACAGG CTATGTCAAA CAGGTCAAGC 70         80         90        100        110       ┌180
     GTATGGTCGT GCACCGTAGA CTGCACGGTA AGCTGCTGGA GATAGCCTTA TCGGCATGAT 130        140        150        160        170       ┌180
     ATGTTTCCAT CAGAAGAGCA CTCTCACGCT GAAAGTTTTG TCCATTCCAA ATTTGAACAA

445AOL2
     ┌─────────┐
          190       │200        210        220        230        240
     GCAGTGACAG TTGCCGCGAT CTACCGAGTA ATTAAGACTC TAGGATGATG CAGGGAGATC 250        260        270        280        290        300
     CTGAGGGTCC TACGCGGATC TCTGCTGGCT ATATAATACG CGCCCATCCT AAAGGTTTTG 310        320        330        340        350        360
     TTTTTAGTTC CAACCGTGGA AAACTTGGCA CAAATCACTG AGCTTTGATT GCACCAAATG

445AOL1
                ┌─────────┐
          370        380       │390        400        410        420
     TCAAACCTAG CAGAGCAAAT ATCTGATGAT GAGGTACTAG GCATCAACTA TCAAGCGCAA 430        440        450        460        470        480
     AAGACTTTCT GAGCAGGCAG GAGTTTTGAT TTCTTATCAC GAGCCATAAG GAGGTGATAG 490        500        510        520        530        540
     GCGCTACACA CACAATCCAA TTCTCAATGT AAAACTGTAG AGCACAGTGA AGCAAGGGGG
```

FIG. 8

```
            550         560         570         580         590         600
     AGAGAAAAAA ACGACTGGCG ATCCTACTTT TGATCGTGAG CCACTCCAGA TCATTTGGTC
                                                     445DOL1
            610         620         630         640  ┌    650         660
     TCACTTTCAC TACATCATCA GATGAATCAT TGTGAACAAC ATCTCAGACT GGATGATGGT 670         680         690         700         710         720
     CTGGTCACTC TCTGAAACAT GGAAAGCAGT TCTAACTGAC AAGTTCAGGA ACCATACTCC 730         740         750         760         770         780
     TTTCTCTCTC TCTCTGGTTC TAACCATATG AACATAAGCT AAATTCTACT GTTTTTTTTG

445DOL2
         ┌  790         800       ┐ 810         820         830         840
     TCCTCTTTCG GTGCAGCTAC AACATGGAAA TGAAACGGAG TAAGAGAAGA AGATAAAAGG 850         860         870         880         890         900
     TTCACCTTTG CTGTTGCTAC CTCTGTACAA TGAGGCCAAC ACCCGACCAA TCGAGCAGGT 910         920         930         940         950         960
     GCTGAATCAA AACCCATGGC GAATCTCATC TCATGTTTTG GGGGGGACAG CCCAATCCAA 970         980         990        1000        1010        1020
     TTCTACGCTT TCTCGAGCGT CCGGGCCAAG TCGACCGNGT TCTTGGCGAT CTTGCAGTTG 1030        1040        1050        1060
     TCGTCGTTCA CCAGAGCCTC GCAGAGGTCG AAACCTGCAG
```

FIG. 9

```
        10          20         30          40         50          60
CTGCAGGCCA  CTGGTATTTA  GAGTGAGAGC  CCTTTTGCAA  TGCCTCTTTG  AACGGCTCTA 70          80         90         100        110         120
ACGCTGGCTC  ATCTTCAAGC  TCTATCAAAC  GATCATAAAA  AATAGCTTTT  TATCGAAAGC

451A2
       130         140        150         160        170         180
CCTCCAAAAA  AGAAAGAGCA  CAAAAAATAT  GGCTTCTAAC  GGATCCTCCT  ACATTTTACT 190         200        210         220        230         240
CACACATCTT  TTAAAATAAA  CACAAGAAAA  CTGTTTTACC  AAATGAATTT  TAAAGTGGTT 250         260        270         280        290         300
CTGATTTTTT  AGAGAAACCA  AAGAGCCAGG  GGAGTCAGTG  CTGAAACTGT  TTTTAGAGGA

C01R1
       310         320        330         340        350         360
ACCCTATTTT  TAGAGGAACC  GGAGCCCTAC  CAAAGGGCCC  TTATTCTAGA  TCGGGCCTAT 370         380        390         400        410         420
AAGTCAGTGA  TCCAAATGCA  AGTGAATTGC  AGGTGAATTA  ATTGTAGATG  ATCTTGTTGT 430         440        450         460        470         480
GTCTGAGGAG  GGCTCAATTG  TAATTAACAT  GTTTAGAGCG  ACTCCAAAAG  ACTGCTATAA 490         500        510         520        530         540
AATTGTTCCC  CAAAACTTAA  TATTAGGGGC  TGATGTAAAA  AANGTTTCCT  AAAAAATTCT
```

FIG. 10

```
       550         560        570         580        590         600
AAATTCACAA  CAGACTACTA  ATAAATTAAC  CCTAAATTTT  TTGAAACAAC  CTAAGCGTGA 451C
       610         620        630         640        650         660
GTCAGAGAAG  ACACATGAAT  TGGGCTTGCA  TTGACAACAT  TCTCGCNACT  GCAG
```

FIG. 13

```
        1                                                       55
MT
B73     TATCGCGAACGTCATGATCCCCACTCGGATGCTTTTTCATGTTATCGTTAGTGGC
OH51    ------------------------------------------------------
TXCO    ------------------------------------------------------
A619    ------------------------------------------------------
H99     ------------------------------------------------------
MO17    ------------------------------------------------------
W153R   ------------------------------------------------------

56                                                     115
MT                                             ACTGTAAATTTGTCTCATA
B73     ATAGAAGGATTAGGGTATATAATTCTCTTACTCTTTATNTC----A---------
OH51    ---------------------------------------------A---------
TXCO    ------------------------------N-------------T--A-------
A619    ------------------------------N-------------T--A-------
H99     ------------------------------N-------------T--A-------
MO17    ------------------------------N-------------T--A-------
W153    ------------------------------N-------------T--A-------

116                                                    175
MT      CCTTATTTATCATCGCAAATGTTTTATTCCCTTTTATGCCACTTGGATCTAATTTCTTAG
B73     ------------------------N-----------------------------------
OH51    ------------------------N-----------------------------------
TXCO    T-----------A-----------N-----------------------------------
A619    T-----------A-----------------------------------------------
H99     T-----------A-----------------------------------------------
MO17    T-----------A-----------------------------------------------
W153    T-----------A-----------------------------------------------

176                                                    235
MT      AACAGATTAGAACATACAA GTTTTTAATCCTTCTATGTCACTGGCGTCAACATAAAAAG
B73     -------------------TT-----N------T--------------A-----------
OH51    -------------------TT-----N------T--------------A-----------
TXCO    -------------------T----------------------------------------
A619    -------------------T----------------------------------------
H99     -------------------T---------------------------------------N-
MO17    -------------------T---------------------------------------N-
W153    -------------------T---------------------------------------N-

236                                                    295
MT      ATAATAAATTGCATCCGGATGATGGCACAGAAGGGGTTAGTATATTTACAATGACAAAAT
B73     -----------------     -------------------------------------N-
TXCO    -----------------     ---------------C----------------------
A619    ------
H99     ------
MO17    ------
W153    ------
```

FIG. 14

```
         1                                                            60
A619  CTCT ACTTTTTAGAGAAACCAAAGAGCCAGGTGAGTCAGTGCTGAAACTGTTTTTAGAG
B73   T---G-----------------G-----------------------------------

61                                                           120
      GAACCCTGTTTTTAGAGGAACCGGAGC        CCTACCAAAGGTCCCTTATTCTAGAT
      -----              -----GCGGAGA----------C-G---------------

121                                                          180
      CGGGCCTATAAATCAGTGACCCAAATGCAAAGTGAATTGCAGGTGAATTAACTGTAGATG
      ------------G-------------------------------------T--------

181                                                          240
      ATGATCTTGTTGTGTCTGAAGAGGGAGGGCTCAATTGTAATTAACATGTTTAGAGCTTTA
      ------------------------------------------------------------

241                                                          300
      GAGCGACTCCAAAAGACTGCTCTAAAATTGTTCCCCAAAACTTAATATTAGGGGCTGATG
      ----------------T-------------------------------------------
```

METHOD AND DEVICE FOR IMPROVED RESTRICTION FRAGMENT LENGTH POLYMORPHISM ANALYSIS

This application is a continuation application of Ser. No. 07/266,970, filed Nov. 3, 1988, abandoned which is a continuation-in-part of co-pending application U.S. Ser. No. 120,309, filed Nov. 13, 1987 abandoned.

FIELD OF THE INVENTION

The invention described and claimed herein relates to restriction fragment length polymorphism analysis, to nucleotide labeling, and to fluorescence detection.

DESCRIPTION OF RELATED ART AND INTRODUCTION TO THE INVENTION

One area in which biotechnology has had a significant impact on plant improvement is in the development of new methods to screen for and identify differentiations of individual plant isolates and varieties. Plant breeding techniques using restriction fragment length polymorphisms for these and other purposes have been well demonstrated. Helentjaris et al., *Plant Mol. Biol.* 5:109-118 (1985). This technique has been used to create RFLP genetic linkage maps, Helentjaris et al., *Theor. Appl. Genet.* 72:761-769 (1986), and the use of such processes in methods to identify and characterize the role of individual plant genes in quantitative trait expression and discriminate gene effects has been documented as well. Neinhuis et al., *Crop Science*, 27:797-803 (1987). These references and all others noted herein are hereby incorporated by reference.

Current RFLP technology typically utilizes the Southern blot technique. Southern, E. M., *J. Mol. Biol.* 98:503-517 (1975). Generally, sample DNA restriction fragments are separated on an agarose gel, denatured in the gel, transferred to a membrane (e.g., nylon) hybridized with labelled probe DNA, washed to remove unbound probe and finally evaluated through, for example, autoradiography. Both the preparation of the membranes with bound DNA and their subsequent hybridization with labelled probes, the latter usually being repeated sequentially many times, are very time consuming steps which can be, therefore, both costly and laborious. Additionally, only one restriction enzyme fragment polymorphic clone can be analyzed for each Southern blot analysis and it normally involves the use of radioactive labelling and subsequent autoradiography. Thus, it will be appreciated that if a technology could be developed which would obtain the same type of genotypic information, albeit more quickly and more economically, in order to make RFLP analyses more amenable for large numbers of samples, it would alleviate these problems and would open up many more opportunities for the application of RFLP technology in both research and industry.

Such a technique is described and claimed herein. In one of its aspects, the invention takes advantage of the use of fluorescent-chromophores as nucleotide labels. These fluorescent-chromophore labels have been used in several analytical applications, most recently in automated DNA sequencers. Connell et al., "Automated DNA Sequence Analysis", *Bio-Techniques* 5:342-348 (1987). In this application, the use of lasers to induce fluorescence of the chromophores allows their detection in small amounts, in the range of femtomole ($10^{-15}$) to anamole ($10^{-18}$). We have made use of this technology in a novel restriction fragment length polymorphism analysis scheme, which can also be performed on an automated basis, to relieve the deficiencies of earlier RFLP techniques in terms of time, labor and cost.

A modification of the above technique is directed to increasing the copy number of genomic polymorphisms detected. Primers are produced which enable the enhancement of regions of test plant DNA corresponding to those regions detected by RFLP probes. By increasing the copy number by several orders of magnitude, analysis of DNA sequence, to the single base level, is made possible.

SUMMARY OF THE INVENTION

In our method, test plant DNA is prepared, cut with a selected restriction enzyme, and denatured to single strand DNA as in conventional RFLP analysis. Existing polymorphic probes, having an average length of about 1000 nucleotides, are sequenced at each of their 5' and 3' ends. A base pair primer sequence from each end of the probe is constructed using conventional DNA synthesis techniques for use in the elongation step described below. A chromophore is selected and attached to each of the base pair primers. These primers are then elongated, preferably with Sequenase ®, a chemically modified phage T7 DNA polymerase which is highly processive, has no 3' to 5' exonuclease activity, and results in virtually no background due to terminations at pause sites or secondary-structural impediments. See Tabor and Richardson, "DNA sequence analysis with a modified bacteriophage T7 DNA polymerase," *Proc. Natl. Acad. Sci. USA* 84:4767-4771 (1987). These elongated primers are run on a denaturing gel together with the original, single-stranded restricted genomic test plant DNA. Hybridization is determined by reviewing the gels with a laser and appropriate detector. No Southern blotting is necessary and, because the chromophores fluoresce to give different emissions spectra, a number of RFLP probes tagged with different chromophores can be run on a single gel at the same time and detected at the same time as well.

This method can be utilized in conjunction with certain technological components to create an automated RFLP analysis system. For example, a broad band laser beam, utilizing wavelengths selected by use of a monochrometer, scans a gel plate that is controlled in its movement by a stepper motor controlled by a computer. The emissions spectrum passing through the gel is detected with an emission spectrograph in combination with an intensified linear photodiode array detector which converts the light received to digital signals. That digital output is transferred to a computer for data acquisition and interpretation. The output from that computer can take any number of forms including spectral data and band identification, and can present data on a chart recorder, printer, or computer screen.

In a modification of the present improvement of restriction fragment length polymorphism analysis, enhancement of the double stranded test plant DNA/-primer DNA is used to increase the sensitivity of the assay to detect sequence variation at the single base level. This modification not only enables detection of size variation due to polymorphisms at the single base level, but also enables sequencing of regions of genomic DNA corresponding to primers complementary to RFLP probes. Essentially, primers are selected and produced in the same fashion as described above except that DNA orientation is reversed. Above, primers are used for extension outward, toward the ends of the test plant restriction fragment. In the present modification, primers are oriented inward, so that extension by DNA polymerase occurs in the region between primers. The copy number of the homologous genomic region in the test plant DNA is increased up to several orders of magnitude. Enhancement not only increases the strength of the signal of the label used, but also increases the amount of DNA which can be used for sequencing. By using primers which allow for such enhancement procedures for detecting RFLP's enables the actual sequence of the RFLP region to be determined. Such enhancement schemes also facilitate automated analysis.

BRIEF DESCRIPTION OF THE DRAWINGS

FIGS. 2, 3, 4, 5, and 6 show the nucleic acid sequence for maize locus 288 and primers used for sequencing this locus.

FIGS. 7 and 8 show the nucleic acid sequence for maize locus 445 and primers used for sequencing this locus.

FIGS. 9 and 10 show the nucleic acid sequence for maize locus 451 and primers used for sequencing this locus.

DETAILED DESCRIPTION OF THE INVENTION

Figure 1:
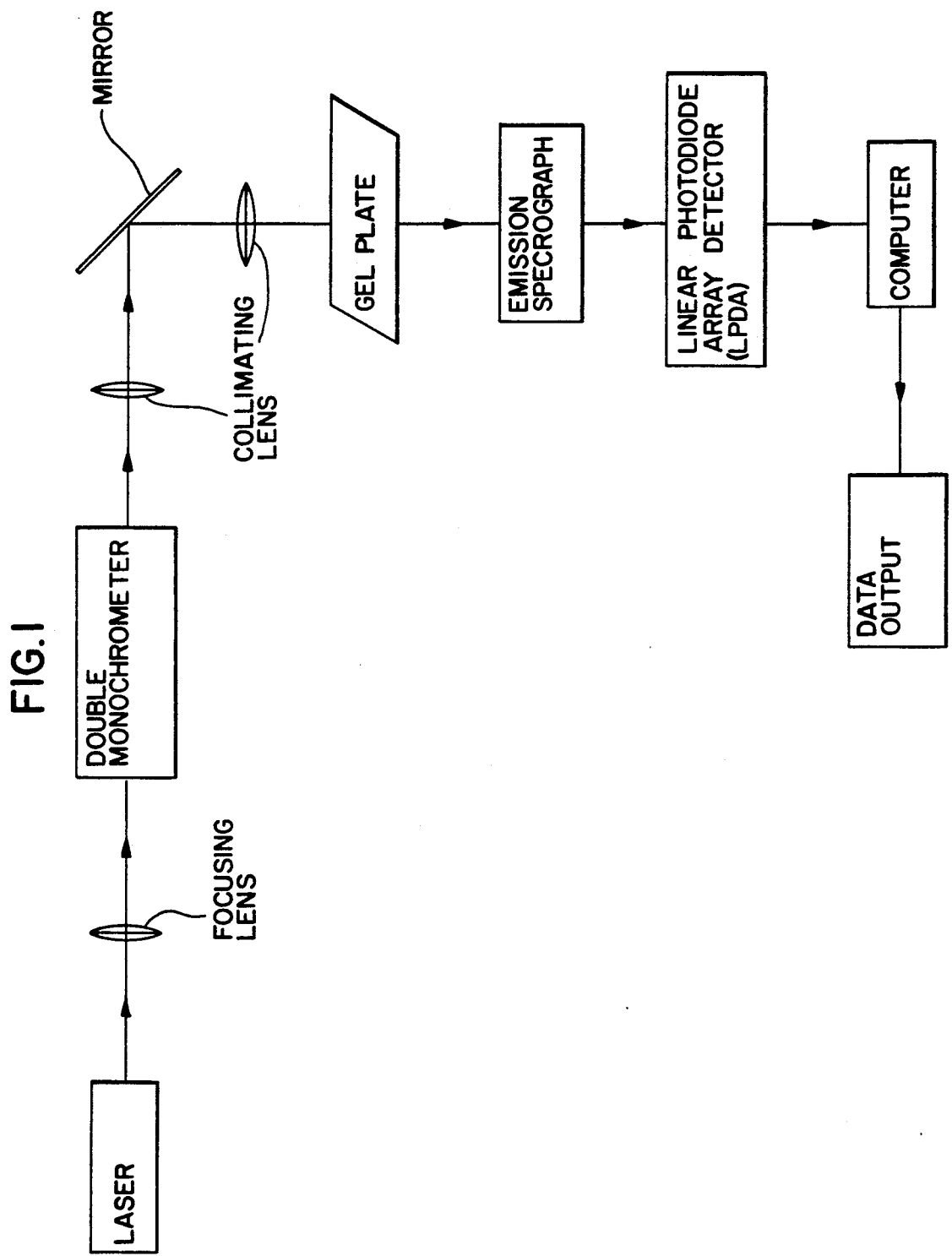
FIG. 1 shows a configuration of a laser detection system for use with the claimed method.

A. Rapid Restriction Fragment Length Polymorphism Analysis

Restriction fragment length polymorphisms (RFLPs) are differences observed between genotypes in the fragment lengths of restriction endonuclease-digested DNA. RFLPs occur as a result of base pair or positional changes in the restriction enzyme recognition sites which flank a chromosomal location and can be detected by hybridization of labelled DNA clones containing sequences that are homologous to a portion of the chromosomal fragment. Hybridization with a unique cloned sequence can permit the identification of a specific chromosomal region (locus).

This technology employs cloned DNA fragments to detect differences between individuals at the DNA sequence level. When genomic DNAs from two genetically distinct individuals are digested with a restriction enzyme, electrophoresed and probed with a labelled DNA clone, polymorphisms in the hybridization patterns sometimes result due to sequence differences between the individuals. The term "restriction fragment length polymorphism" has been coined to describe this variation.

Differences in fragment lengths which are revealed, for example, by agarose gel electrophoresis, function as alleles of that RFLP. Thus, RFLPs can serve as genetic markers in a manner analogous to conventional morphological or isozyme markers. Unlike most genetic markers, however, they are not the products of transcription and translation. Additionally, RFLPs possess certain additional advantages over previously available genetic markers. First, RFLPs reflect existing differences between genetically distinct individuals. The potential number of RFLPs for all practical purposes is thus unlimited, as digestion of the genomic DNA of any higher eukaryote with a six base recognition enzyme will generate more than a million fragments, many of which can be polymorphic. Additionally, over 100 different restriction enzymes have now been described, each of which may generate a new and different set of fragments. The utility of isozyme markers or morphological markers in studies is frequently limited by a lack of informativeness in lines of interest or by an insufficient availability or chromosomal distribution of the loci.

Many of the potential applications and theoretical advantages of RFLPs compared to more conventional phenotypic or isozyme marking systems have been previously described. Helentjaris et al., *Plant Mol. Biol.*, supra. In one application of the use of RFLP markers in plant studies, genetic linkage maps based on these markers have been constructed. Helentjaris et al., *Theor. Appl. Genet.*, supra. For example, over 300 RFLPs in maize have been arranged into linkage groups. The locations of the maize RFLP loci have been correlated to the conventional maize genetic map by analyzing the inheritance patterns of the RFLPs in maize lines monosomic for different chromosomes. Helentjaris et al., *Proc. Nat. Acad. Sci. USA* 83:6035-6039 (1986), by establishing linkage relationships with isozyme markers, cloned genes, and morphological markers with previously identified chromosomal locations, Wright et al., MNL 61:89-90 (1987), and by analyzing inheritance patterns in B-A translocation stocks. The use of RFLPs to dissect multigenetic traits into their individual genetic components has also been described. A genome, or portion thereof, saturated with RFLPs or probed with select RFLP markers, all of which can be evaluated together in individual plants, has been found to give the resolution necessary to break down traits of complex inheritance into individual loci, even those under a significant environmental influence. The procedure is equally workable with dominant or recessive traits and can be used to accelerate introgression of desired genes into a commercially acceptable cultivar. Nienhuis et al., supra.

Accordingly, it will be appreciated that the many utilities of RFLP analysis in plant studies enhance the desirability of utilizing that technology in a manner that is as efficient, fast, and cost effective as possible. In the improvement described and claimed herein, a novel method for RFLP analysis is set forth which utilizes fluorescent-chromophores in a unique manner. By this method, which involves the use of lasers to induce fluorescence of chromophores tagged to RFLPs, the cost, labor, and time associated with Southern blotting and radioactive labelling is significantly diminished. Furthermore, through the use of multiple chromophores with different emission frequencies, each tagged to a different RFLP, one can detect the presence of multiple target compounds simultaneously. Hence, instead of having to hybridize a Southern blot repeatedly with different probes all tagged by the same radioactive compound, e.g., $^{32}P$, one can hybridize a blot with a number of probes simultaneously, each bearing a different chromophore.

Although this strategy may be used for detection of chromophores hybridized to targets immobilized on a Southern blot solid matrix, such as a nitrocellulose or nylon membrane, it is anticipated that this could result in a loss of sensitivity of several orders of magnitude in comparison to detection of such chromophores in solution or on a gel. This may well be enough of a loss in sensitivity to preclude practical detection of single-copy DNA sequences in a higher eukaryotic such as humans or corn. Furthermore, as noted above, one would still practice the steps of transferring the restricted DNA fragments in the gel to a membrane, hybridizing the RFLP probe to the membrane bound DNA fragments, and removing the unbound probe.

The following alternative method circumvents the potential problem with detection on solid matrices, which has the added benefit of obviating the need to transfer the genomic DNA fragments from the gel. Detection may be carried out in the gel, thus significantly reducing the number of steps in the entire process and allowing one to assay multiple probes simultaneously on single samples.

In this method, two single strand DNA primers of about 15 to about 20 nucleotides, or of any other length sufficient to serve as a DNA primer, are constructed using sequence information from a cloned probe which is known to reveal polymorphisms through conventional Southern analysis. By sequencing in from each end of the cloned probe a short distance, one can deduce a sequence at each end that will extend outward from the probe ends in a 5' to 3' manner. While the probe may not actually include the polymorphic region of the genomic fragment created by restriction enzyme digestion, it does lie internal to both of the ends of the informative fragments. The two primers, if extended out into the rest of the genomic DNA fragment from the cloned ends, will eventually stop at the ends of the polymorphic genomic fragment. At least one of these two extensions must contain the polymorphic region and, indeed, both could prove to be informative.

Once these primers have been produced for each probe, they are tagged using chromophores as described below. The attachment of chromophores, clearly, must not interfere with hybridization of the primer to the DNA of its complementary sequence and it must also not interfere with extension of the primer from the 3' end by a DNA polymerase.

The genomic DNA samples to be tested are digested with the appropriate restriction enzyme which will create polymorphic or informative fragments. The total digest is then mixed with the chromophore-tagged primers, denatured into single strands by heating for about three to five minutes, and immediately transferred to a 37° C. bath and left for a short time. The period should be long enough to allow the denatured DNA mix to cool to 37° C. but not so long that many of the high copied sequences present in the genomes of all higher eukaryotics will be able to renature. A period of about several minutes in duration will be sufficient. Because renaturation of single strand DNA into double strand DNA is dependent upon both time and the concentration of the sequences involved, and because the concentration of the unique sequences in these genomes is extremely low, very few of them will have reannealed within this time period. On the other hand, the complementary primers can be added at very high concentrations, for example several nanograms, which will represent a several thousand-fold excess of primer to complementary genomic DNA sequences. These would therefore anneal almost immediately to their complementary genomic sequences and form a short double strand region.

In the next step, a polymerase, preferably modified T7 DNA polymerase ("Sequenase ®"), is added along with all four individual bases, dATP, dCTP, dGTP, and dTTP, and an appropriate buffer. This enzyme has the ability to quickly copy very large single strands of DNA using small primers. While other studies have used the large fragment of DNA polymerase (Klenow) to amplify and detect various small genomic sequences (on the order of 100–200 bases), this approach may prove impractical for the larger fragments (which can be on the order of 2000–12000 bases) that are necessary for human and plant RFLP analysis. The Kenlow fragment rate of copying may be too slow and the denatured strands might well reanneal due to the presence of repetitive sequences before complete copying had been accomplished. Modified T7 polymerase, on the other hand, has a very fast rate of copying and very high processivity, factors which allow it to copy a 10,000 base template in a matter of a few minutes. In our method, modified T7 DNA polymerase should, in a relatively short time, extend off the 3' end of the primer all the way to the end of the genomic fragments. The enzyme should also extend any other annealed sequences that may have been formed. Only those which have been extended off chromophore-tagged primers, however, will be detected in our method, as described below.

Two avenues for detection of the reaction products may be followed. First, any remaining single strand DNA may be digested with S1 nuclease, which would remove the opposite single strand DNA end of the extended fraqments leaving it completely double-stranded. This would also serve to destroy any unused primers which, as described above, would typically have been added in vast excess. Only those strands which had been copied to double strand DNA would then be recovered in the following isolation step. That isolation step could be accomplished by any of a number of known techniques, such as ethanol precipitation or mini-column chromatography. The isolation fragments are then loaded onto a standard neutral agarose gel and separated by size through electrophoresis.

Alternatively, the total reaction product following treatment with modified T7 DNA polymerase could be denatured into single strands and analyzed by electrophoresis on a denaturing agarose gel system. The former method is preferred because it will remove unused chromophores which might result in a smearing of the gel and a resultant complication of the final analysis.

After electrophoresis in either of the above-described methods, the gel may be scanned by a laser to excite the chromophores to fluoresce, which fluorescence can be detected by a linear photodiode array detector. By examining the data for the emission spectrum peculiar to each chromophore, the polymorphic regions of the test DNA may be detected. Furthermore, once the primers have been prepared in sufficient amount, for example, for hundreds of assays, the remaining steps of digestion, denaturing, extension, electrophoresis, and detection could be accomplished in a very short period of time. By way of illustration, it is envisioned that the entire process could be carried out in one working day for about 20 probes and a large number of genomic DNA test samples. To accomplish this same amount of work using conventional Southern blot technology could take up to several months, even under ideal conditions. Plainly, the time and expense saved will prove to be invaluable in the utilization of such RFLP analyses.

DNA sequencers utilizing laser induced fluorescent detection and chemical modification of DNA fragments to attach fluorophores are currently commercially available. See Prober et al., *Science* 238:338–341 (1987). Although techniques applied in DNA sequencing are sensitive enough to replace $^{32}$P-autoradiography, they can only be detected at selected fluorescent emission wavelengths. Thus, as described in Prober et al., supra, only up to 4 fluorophores with emission maxina close to one another were used.

As indicated above, by coupling a fluorometric photodiode array detection system, e.g., Gluckman et al., Anal. Chem. 57:1546–1552 (1985), and laser excitation of RFLP fragments labelled with different fluorophores whose emission spectra are unique, one can not only detect low concentration of DNA fragments in a separating gel media ($10^{-16}$ to $10^{-18}$ mole) but can also distinguish one fluorophore from another through computer aided spectral comparison. This allows one to simultaneously analyze DNA fragments generated by a single restriction enzyme in a single lane of gel with multiple DNA probes.

An optical system for use in our method is modified from Gluckman et al., supra. A post-run gel is mounted on a quartz plate (20×20 cm). The plate is moved along X-Y coordinates, a monochromatic laser beam will excite a band representing DNA fragments containing a particular fluorophore (DNA probe). The entire emission spectrum passing through the quartz plate is detected using an emission spectrograph coupled to an intensified linear photodiode array (LPDA) detector. The output from the intensified LPDA is converted to digital signals by a detector controller/interface which then transfers them to a computer. The rapid transfers of digital signals allows multiple scannings of the same band which can reduce background noise level and increase signal level. A computer aided spectral library of standard fluorophores will subsequently correlate the band to the corresponding DNA probe. Thus, RFLP fragments will be identified by their fluorescent probe types as well as by X-Y coordination of the gel plate. Although technologies exist for fluorometric photodiode array detection, computer programming for spectral acquisition and comparison and mechanical gel scanning devices, none of these techniques have been combined to detect multiple DNA probes for RFLP analyses as described herein.

Set forth below in greater detail are procedures relative to the production of primers, chromophore selection, primer labelling, digestion of genomic DNA, denaturing and annealing of template and primers, extension reactions, and S1 nuclease treatment. It will be appreciated that other means for achieving the same results as those of these protocols will be possible and useful.

It is presently preferred to produce primers using cloned probes that reveal polymorphisms in conventional Southern blot analysis. Such an RFLP probe is typically smaller than the fragments it will detect in Southern blot analysis, although this is not necessarily so and neither is it a requirement. An RFLP probe, selected at random or otherwise, may be cloned into a plasmid, such as pUC18, which has a multiple cloning site (MCS) and is amenable to DNA sequencing into the ends of the inserts using primers complementary to the ends of the MCS. With this system, one can easily sequence in a few hundred bases from each end in one run. This sequence information can then be used to produce two primers which, when extended on genomic DNA, would result in an extension product that covers any polymorphic region detected by the original cloned probe. Using any 20 base sequence as one primer, for example, it would extend in one direction to the end of the template. If the complementary sequence is then used as a second primer, it would extend in the opposite direction to the other end of the template. Accordingly, two useful primers may be selected from only a short sequencing effort. It may be that a selected primer would not be useful if its sequence were found at other locations in the genome. Although this is possible it is unlikely because the probes that are used in these analyses are selected on the basis of their relative uniqueness. Of course, if the selected primer appeared to reveal more than one sequence in the later analysis, another primer sequence could be tried from another area of the cloned probe.

Oligomeric (20 mer) deoxyribonucleotides were synthesized according to known techniques in solid phase phosphoramidite chemistry. Following oligodeoxyribonucleotide production, these synthesized nucleotides were chemically modified at their 5'-termini by attaching a primary alkylamine group, N-monomethoxytrityl-methoxy-N,N-diisopropylamino-phosphinyl-3-amino-1-propanol, also by known techniques. The modified oligodeoxyribonucleotides were isolated, purified and labelled by coupling commercial amine selective fluorescence dyes. Fluorescence labelled oligodeoxyribonucleotides were purified by HPLC and used as primers for different restriction enzyme fragment clones.

The synthesis of modified oligodeoxyribonucleotides was done according to B. A. Conolly (Nucleic Acids Research Vol. 15(7):3131, 1987) with some modification. Oligodeoxyribonucleotides were made using an Applied Biosystem DNA synthesizer. Three amine selective fluorophores, dansylchloride (Aldrich Co.), FITC (fluorocein-5-isothiocyanate), and NBD-fluoride (4-fluoro-7-nitrobenz-2-axa-1,3 diazole) (Molecular Probes) were selected to label the modified oligodeoxyribonucleotides.

N-monomethoxytrityl-0-methoxy-N,N-diisopropylaminophosphinyl-3-amino-1-propanol, for use in linking one of the above fluorophores to the 5' end of a synthetic oligodeoxyribonucleotide primer, was prepared as follows. P-anisyldiphenylchloromethane (7.72 g, 25 mmol) and 3-amino-1-propanol (7.5 ml, 100 mmol) were dissolved in dry CH$_2$Cl$_2$ (molecular sieve #3A and Na$_2$SO$_4$ anhydrous filtered) 50 ml and 25 ml, respectively. For over one hour, P-nisyldiphenylchlormethane solution was added dropwise into the ice cold solution of 3-amino-1-propanol with constant mechanical stirring. The mixture was left ½ hour at room temperature, then washed two times with 5% NaHCO$_3$ (50 ml) followed by the same volume of saturated brine. The washed CH$_2$Cl$_2$ solution was dried over Na$_2$SO$_4$ (anhydrous), and concentrated vacuo. N-monomethoxytrityl-3-amino-1-propanol was crystallized by dissolving the concentrated mixture in Et20: Hexane, then chilling in liquid nitrogen. Crystals were collected, washed with cold hexane until all the yellow coloration disappeared. White crystals of N-monomethoxytrityl-3-amino-1-propanol were recrystallized in cold Et20 and dried over Si-gel in vacuo. Over 4.5 g of crystals were obtained. The product was examined by TLC, 1H-NMR and FAB-MS, and compared to the literature data.

Following completion of synthesis of the desired intermediate, N-monomethoxytrilyl-3-amino-1-propanol, an Si-TLC plate was developed once with CH$_2$Cl$_2$:CH$_3$OH:ET$_3$N (97:2:1, v:v:v) and visualized by vanillin H$_2$SO$_4$. A starting compound, P-anisylchlorodiphenylmethane, and the final product, N- monomethoxytrityl-3-amino-1-propanol, have Rf valves of 0.9 and 0.58 respectively. The reaction product was characterized by FAB(+)MS and 1H-NMR (200 MHzDC13, TMS). The FAB(+)MS spectrum showed a quasi-molecular ion (M+H)+ of M/z 348 along with a major fragment ion peak of m/z 273 (C2H17O)+ which suggested the molecular formula of C23H25O2N. 1H-NMR spectrum of N-monomethoxytrityl-3-amino-1-propanol showed 7.45–7.15 (m, 14H), 6.81 (d, 2H), 3.89 (t, 2H), 3.78 (s, 3H), 2.34 (t, 2H) and 1.69 (ddd, 2H). These values are in very close agreement with those of the literature values. Slight Rf value differences between experimental and literature data might be due to slight difference TLC conditions. These spectral data strongly suggested that the reaction mixture (a 65% yield) was the desired intermediate, N-monomethoxytrityl-3-amino-1-propanol.

N,N-diisopropylethylamine (1.9 ml, 10 mmol) was added to the $CH_2Cl_2$ solution of N-monomethoxytrityl-3-amino-1-propanol (1.73 g, 5 mmol, in 10 ml of dry $CH_2Cl_2$) and the mixture was cooled on ice. For over a 5 min. period, N,N-diisopropylmethylphosphoramidic chloride (0.97 ml, 5 mmol) was added dropwise with constant stirring. The reaction mixture was left in the ice bath for 10 min. At the end of 10 min., $CH_3OH$ (1.0 ml) was added to it and left at room temperature for another 10 min. Additional $CH_2Cl_2$ (25 ml) was added and washed 2× with 5% NaHCO3 (50 ml) and 1× with saturated brine (50 ml). The $CH_2Cl_2$ solution was dried over $Na_2SO_4$ (anhydrous), and concentrated in vacuo. N-monomethoxytrityl-0-methoxy-N,N-diisopropylaminophosphinyl-3-amino-1-propanol was purified from the reaction mixture through silica gel flash column chromatography. 1.67 g of clear colorless oil was obtained by in vacuo concentration of appropriate column fractions. The compound was characterized by TLC, 31P-NMR and FAB(+)MS.

The completion of the above reaction was monitored once again by TLC. TLC plates (Si) were developed once with Hexane:Et3N(9:1, v/v) and viewed under a U.V. 254 nm lamp. The starting intermediate compound, N-monomethoxytrityl-3-amino-1-propanol, and the final product, N-monomethoxytrityl-O-methoxy-N,N-diisopropylaminophosphinyl-3-amino-1-propanol, have Rf valves of 0.05 and 0.63 respectively. The final product was purified by flash column (Si) chromatography and characterized by FAB(+)MS and 31p-NMP (CDC13/Eb3N 9;1, 81.3 MHz, $H_3PO_4$). The FAB(+)MS spectrum of the final product showed a quasimolecular ion (M+H)+ of m/z 509 which suggested the molecular formula C3OH41O3N2P. 31p-NMR spectrum of the final product showed a single peak at 147.73 ppm down field from $H_3PO_4$. This value is comparable to the literature value of 148.29 ppm. These spectral values identified the final reaction product as N-monomethoxytrityl-O-methoxy-N,N-diisopropylaminophosphinyl-3-amino-1-propanol.

Flash column chromatography was performed as follows. Silica gel (40 μm) was wetpacked ($CH_2Cl_2$, 15 cm×3 cm) into a flash column. The packed column was washed 2× with hexane (200 ml) and 1× with hexane-Et3N (3:1, 200 ml). The reaction mixture was dissolved in a small volume of the eluting solvent (Hexane-Et3N, 8:1). Approximately 10 ml volume fractions were collected.

Synthesis of deoxyribonucleotide having a 5′-terminus modification with N-monomethoxytrityl-O-methoxy-N,N-diisopropylaminophosphinyl-3-amino-1-propanol was accomplished by the following method. Oligodeoxyribonucleotides (20 mer) were prepared using standard solid phase phosphoramidite methods on a scale of about 1 μm of bound first nucleoside. After the required sequence synthesis was compiled, an extra round of synthesis was carried out using N-monomethoxytrityl-O-methoxy-N,N-diisopropylaminophosphinyl-3-amino-1-propanol (12.7 mg in acetonitrile, 25 μm) and 60 μm of tetrazole. Following this coupling, oxidation of phosphite triester with $I_2/H_2O/THF$, demethylation with thiophenol and cleaving and deblocking of the base protection group with $NH_3$ were done without deprotecting the newly introduced $NH_2$ group. The crude monomethoxytrityl protected oligonucleotides were purified by reversed phase HPLC. Purified oligonucleotides were dissolved in 2 ml of 80% HOAc for two hours to deprotect the amine group. At the end of two hours, HOAc was removed by evaporation and the oligomers with propylamine group was dissolved in a small volume of water.

To couple the modified oligonucleotides to the fluorophores, an aqueous solution of the modified oligonucleotides (0.01–0.25 μm, in 100–500 μl) was mixed with an equal volume of 5% $NaHCO_3/Na_2CO_3$ buffer (pH 10). NBD-fluoride and FITC were dissolved with dimethylformamide (100 μg/ml) and dansylchloride was dissolved in acetonitrile (100 equivalent to oligomer, 1–25 μm). These fluorophore solutions were added to the solutions of modified oligonucleotides and incubated over three hours. Fluorophore labelled oligonucleotides were purified by reversed phase HPLC for use in subsequent RFLP analyses.

B. Enhancement of Test Plant DNA/Extended Primer DNA

Methods to enhance the amount of test plant DNA may be used to both increase the sensitivity of the assay as well as to detect sequence variation at the single base level. Using such a modification, not only can minute size variation be detected, but alterations in the DNA sequence itself can be characterized. This is significant because among plants, much of the variation may constitute changes at the single base pair level. Differences among genomic DNA fragments as a result of these changes could be too small in size to praticably detect by Southern blotting or gel electrophoresis. Also, variation may constitute base pair substitutions which could result in no detectable size alteration, and could also not prevent binding of probe (or primer) except under the most stringent of hybridization conditions. In addition, in extending the primer used in the above example using T7 DNA polymerase, minor alterations of DNA sequence in the part of the sequence extended using T7 are not detectable. The frequency of binding of the primer DNA to the test plant DNA is fairly low because the probes, from which the primers are derived, are chosen on the basis of their low copy number in the plant genome. Thus, one object of the present modification is to selectively increase the amount of test plant DNA bound to the extended primer.

In order to detect variation at the single-base level, and at the same time make the present analysis more amenable to automation techniques, the preferred method is one in which the test plant DNA to which primer has been bound is enhanced up to about a million fold. This increase in the amount of test plant DNA enables, for example, direct sequencing of the enhanced segment so that single base pair changes can be detected and characterized, amplification of the signal (e.g., fluorescence from a chromophore label attached to the primer) by enhancement of the extended primer/test plant DNA so that even very low original concentrations may be detected. Moreover, with the increase in signal, less sensitive detection devices are required.

The polymerase chain reaction technique or "PCR", is one method which may be used to selectively amplify the extended primer DNA/test plant DNA hybrid. PCR is described by U.S. Pat. Nos. 4,683,195 and 4,683,202, both of which are herein incorporated by reference. Using this technique, only the double-stranded extended primer/test plant DNA is amplified; unbound single stranded DNAs are not incorporated and remain unchanged.

In order to use the PCR technique for amplifying the present DNA fragments of interest, it is necessary to ensure that the desired fragment is short enough to be accurately amplified. PCR is for the most part limited to amplification of segments of less than approximately 1 Kb. The test plant genomic fragments which exhibit polymorphic characteristics however are frequently over 1 kb in their entirety, as the polymorphisms themselves may lie beyond the termini of the approximately 1 Kb RFLP probes we have used.

To solve this problem the focus on the analysis was shifted from the RFLPs themselves (i.e., the differences in restriction fragment lengths among plant DNA) to the variation in the sequence of the DNAs among plants tested. These concepts are related in that sequence variation results in RFLP presence, however, analysis of RFLPs alone does not typically indicate the nature of the variation of the sequence itself. In other words, analysis is no longer limited to the change in length of restriction fragments, but also includes sequence changes which cause the change in length. Also included are sequence changes, such as base substitutions, which may cause no change in sequence length as well as minute sequence additions and deletions which produce changes in length which are not practicably detectable.

In order to enhance test plant DNA to which primer has been bound, the same basic technique as above was used. However, instead of producing two primers which each can be extended outward toward the ends of the test plant restriction fragment, primers which can be extended inward—that is, each extended toward the other and thus toward the intervening region of the test plant—are produced. In this way, the double stranded region to be amplified is limited to the size of the probe from which the primers are derived. Because the probe typically is comprised of fewer then 1 Kb, amplification using PCR is possible.

After enhancement, there may be up to millions of copies are produced of what would otherwise be very low copy number genomic DNA restriction fragments, thus providing enough DNA for sequencing. Because the region between primers, filled in by DNA polymerase, may differ among isolates or varieties, differences in actual sequence can be characterized.

Also, by amplification of the region between primers of the double-stranded extended primer/test plant DNA, using labelled oligomers, the signal of the label may be coincidently amplified. This may significantly reduce the complexity of the detection scheme.

After amplification, various techniques for detecting sequence variation are possible. The following four detection techniques are set forth as examples, but other detection techniques will be apparent to those skilled in the art.

A size polymorphism created by a rearrangement within the amplified region could be analyzed directly on a gel or a column, using the label on the amplified region as the means of detection. While this technique will increase the strength of the signal, single base pair changes will not likely be detected.

If a sequence change creates a new restriction site within the amplified region, predigestion of the test DNA (bound to the inward-extended primer) prior to amplification would block amplification. The differences in amplification among test plants would indicate the nature of the alteration in sequence. This "+/−" type assay enables automation easily; however, reliance is placed upon the fortuitous creation or destruction of restriction sites.

Another technique which can be used to identify whether or not test plant genomic DNA possesses a sequence corresponding to sequences derived from extended primers is to use stringent hybridization conditions. Under such stringent hybridization conditions, which are well known in the art, there is discrimination against hybridization between mismatched oligomers. One could amplify with unlabelled oligomers, heat denature, and then hybridize under stringent conditions, with labelled internal oligomers which match all of the various sequence variations. In this "+/−" assay, whether or not a particular test plant genomic fragment contains certain sequences can be ascertained.

Using fairly stringent hybridization conditions in the annealing step of the enhancement process also provides a practical assay to determine whether a test DNA fragment contains even single base pair changes. Essentially, different primers are used, one fixed at one end of the region to be amplified and two others, each of which end (at the 3' end) in different bases. Each of the two variable primers also is labelled with a different label. For example, one could be tagged with a red fluorescing chromophore, another a green fluorescing chromophore, etc. The fixed primer acts as the opposite end of the complete oligonucleotide produced by filling in the region between the labeled primer (with the variable 3' end) and the fixed primer itself. The "fixed" primer is annealed with the test plant DNA, under stringent hybridization conditions, along with the variable oligonucleotides, each having a different base pair sequence at their respective termini, and each bearing a different label.

Next, the bound "fixed" primer, as well as any bound variable primer, are extended toward each other by use of any DNA polymerases, such as Taq polymerase, infra. The test plant DNA between the primers is then amplified under conditions allowing for incorporation of the label of the original primer in all copies. Because a primer with a 3' mismatch is likely to cause extremely inefficient extension, then only an oligomer with 3'termini properly corresponding to that of the test DNA is likely to allow for amplification. The amplification products could be analyzed to determine what label is present, e.g., red chromophore, green chromophore, both, etc. The different labels detected could indicate, for example, whether a test plant is homozygous parental or a heterozygous genotype.

A further modification of the latter detection method is to vary the size of the amplified region on the basis of the distance between the fixed and the labelled, variable primer chosen. By varying this distance between several different loci, and amplifying them all simultaneously (which can be performed in a single vessel), the mixture could be run on a gel and analyzed. Each of the loci with variation at the 3' end of the various primers would then be detected at different molecular weight points on the gel by detecting the different chromophores, or other labels used. Thus, multiple loci could be screened in a single gel lane using only two different tags.

Set forth below in greater detail are procedures for enhancement, and sequencing of genomic DNA. It will be appreciated that other means for achieving the same results as those of these protocols will be possible and useful.

Enhancement for Direct Sequencing of Loci 288 and 451 from Maize Cultivars

The following is a protocol used for polymerase chain reaction amplification of genomic corn DNA to which two different primers are bound. The corn lines tested are indicated below, by their conventional designation. All corn lines tested are available from both public and commercial sources.

The primers used were manufactured by conventional techniques using RFLP probes from the maize loci as indicated. Helentjaris, Trends in Genetics 3:217 (1987). The DNA sequences of the primers used are shown in FIGS. 2 through 10. FIGS. 2–6 show the nucleic acid sequence for maize locus 288. The sections of the locus used for primers are underlined, and specific primers are indicated. FIGS. 9 and 10 show the DNA sequence for maize locus 451, again indicating the specific primers. The primers were manufactured, by conventional methods, so that their orientation allows for extension by PCR between the primers used.

The following genomic DNA/primer mix was used:

| Tube: | Genomic DNA, 5 µg. | Primer #1, 100 µM | Primer #2, 100 µM |
|---|---|---|---|
| 1 | 13.5 µl, #5 A619 | 1 µl 288A | 1 µl 288EOL1 |
| 2 | #21, Mo17 | 1 µl 288A | 1 µl 288EOL1 |
| 3 | #28, H99 | 1 µl 288A | 1 µl 288EOL1 |
| 4 | #33, W153R | 1 µl 288A | 1 µl 288EOL1 |
| 5 | #34, Oh51 | 1 µl 288A | 1 µl 288EOL1 |
| 6 | #47, B14AHt | 1 µl 288A | 1 µl 288EOL1 |
| 7 | #113, B73Ht | 1 µl 288A | 1 µl 288EOL1 |
| 8-14 | #113, B73Ht | 1 µl 288AR | 1 µl 288BOL1 |
| 15-21 | #113, B73Ht | 1 µl 451AH3 | 1 µl 451CH3 |

Two opposing primers were used per test plant genomic DNA.

The protocol for the PCR amplification was performed using the Taq polymerase manufactured by Perkin Elmer Cetus (Norwalk, Conn.). The procedure set forth in the product brochure was followed, and such procedure is herein incorporated by reference. See also. Li, et al., Nature 325:414 (1988) for a description of the amplification of DNA sequences.

RNA in the unpurified genomic DNAs was digested by adding 10 µl of the following:

| Rx (24X) | |
|---|---|
| dH$_2$O | 1248 µl |
| 10X PCR Buffer | 216 |
| DMSO | 240 |
| gelatin | 48 |
| RNase | 4.8 |

The mixture was allowed to incubate for 5 minutes at room temperature, and then for five minutes at 95° C.

The polymerase chain reaction mix, using Taq polymerase as provided in the amplification kit, supra, was as follows:

| Rx (23X) | |
|---|---|
| dH$_2$O | 13.8 |
| 2.5 mM dXTPs | 184 |
| 10X PCR Buffer | 23 |
| enzyme | 9.2 |

The polymerase chain reaction was allowed to proceed through 30 cycles, each of 2 minutes at 93° C., 2 minutes at 55° C., and 4 minutes at 72° C., with a last 10 minute extension cycle. The above cycle was found to allow for sufficient binding of the primer without significant reannealing of the complementary strands of the genomic DNA.

10 µl of each amplification product was run on an agarose gel, prepared conventionally and stained with ethidium bromide. This gel is at FIG. 11. This gel shows that the 288 primers worked in a subset of the lines tested. The 451 primers show a band of about 300 bp. Line B14 a showed a larger fragment with the 288A primer and 288 EOLI primer than did the other lines.

The rest of the samples were prepared for sequencing, (see infra). 23 µl of 5× PCR stop mix was added, and the samples were incubated at 50° C. for 60 minutes. The samples were phenol and chloroform extracted 1× each, and Centricon (Amicon Corp., Lexington, Mass.) dialyzed 3×. The samples were then precipitated with ammonium acetate, and resuspended in 10 µl of buffer.

PCR Amplification Using Multiple Cultivars and Amplifiers

Here, different cultivars were tested with different primers. In addition, different amounts of test plant DNA were used:

| Tube | Substrate | Primer #1 | Primer #2 | dH$_2$O |
|---|---|---|---|---|
| 1 | #21 Mo17, 1 µg | 288A | 288EOL1 | 25.31 µl |
| 2 | #21 Mo17, 5 µg | 288A | 288EOL1 | 14.5 |
| 3 | #21 Mo17, 10 µg | 288A | 288EOL1 | 1 µl |
| 4-6 | #21 Mo17, 10 µg | | | |
| 7 | MT 1 µg | 288A | 288EOL1 | 25.3 |
| 8 | A619 | 288BOL1 | 288EOL1 | 25.3 |
| 9 | Mo17 | 288BOL1 | 288EOL1 | 25.3 |
| 10 | H99 | 288BOL1 | 288EOL1 | 25.3 |
| 11 | W153R | 288BOL1 | 288EOL1 | 25.3 |
| 12 | Oh51 | 288BOL1 | 288EOL1 | 25.3 |
| 13 | B14A | 288BOL1 | 288EOL1 | 25.3 |
| 14 | B73 | 288BOL1 | 288EOL1 | 25.3 |
| 15-21 | as above but with | 238A | 238COL1 | 25.3 |

The same protocols as above were used for PCR amplification; and 10 µl was removed and run on an agarose gel, FIG. 12. The gel shows uniform amplification, as detected by the ethidium bromide stain, in the inbred lines. Moreover, it appeared that 5 µg of DNA promoted optimum amplification, and that there was an decrease in amplification when 10 µg was used. The polymorphism in B14A, as in FIG. 11, was again detected.

Effects of Increasing Amounts of Test Plant DNA, Varying the Number of Amplification Cycles, and Cleaning-Up of Test Plant DNA on the Degree of Enhancement Genomic DNA from corn inbred MT was isolated by standard techniques and used for all samples. The primers 288BOL1 and 288EOL1 were both used in each sample. The "dirty" DNA below indicates MT genomic DNA without pre-treatment to remove proteins or other extraneous materials. "Clean" DNA is an RNase-treated sample of genomic DNA, phenol and chloroform extracted, 1× each. After PCR amplification, the sample was Centricon dialyzed 4 more times and ammonium acetate precipitated. The DNA pellet was washed once with 80% ethanol.

The number of PCR cycles was also varied, with samples undergoing either 30 or 35 cycles. The samples were used:

| | |
|---|---|
| 1 | 1 µg of dirty-DNA-35 cycles of PCR |
| 2 | 5 µg of dirty-DNA-35 cycles of PCR |
| 5 | 1 µg of dirty-DNA-30 cycles of PCR |
| 6 | 5 µg of dirty-DNA-30 cycles of PCR |
| 8 | 1 µg of dirty-DNA-30 cycles of PCR, added enzyme at cycle 15 |
| 9 | 1 µg of clean-DNA-30 cycles of PCR |
| 10 | 5 µg of clean DNA-30 cycles of PCR |
| 15 | reused a centricon column sample is same as 8 |

The PCR amplification used was as described, supra.

Electrophoresis gel analysis of the samples indicates that use of 5 µg of test DNA increases the amount of DNA amplified over that obtained from using 1 µg test DNA. Pre-PCR clean-up showed a slight but non-significant increase in amplification. There was no difference in amplification when samples underwent 35 PCR cycles, from that detectable from 30 cycles.

Direct Sequencing of Amplification Reactions

Presented is the preferred method for sequencing the amplification product. The samples used here are samples 8-14, prepared as described in the section "PCR Amplification with Multiple Cultivars and Amplifiers," supra.

Samples 8-14 were each extracted once with 25:24:1 phenol: $CHCl_3$:isoamyl alcohol, and then once with 24:1 $CHCl_3$:isoamyl alcohol. The samples were filtered through 30 kDa Centricon ultrafilters four times, successively diluting with 2 ml water with each filtration. The final resulting retentive was collected and $NH_4OAc$ was added to a final concentration of 2M. Two volumes of cold ethanol was added, and the mixtures were chilled overnight at −20° C.

DNA was sequenced using a Sequenase ® kit a modified T7 DNA polymer (U.S. Biochemical Corp., Cleveland, Ohio) according to the manufacturer's specification, which is herein incorporated by reference. PCR template DNA was dissolved in 10 µl buffer after sedimenting and washing with cold 70% ethanol. One µl was sampled for electrophoresis, which indicated a recovery of approximately 150 to 300 ng in most of the samples.

The remaining 9 µl were heated in a boiling water bath 5 minutes and 3 µl of the following primer/buffer mixture, warmed to 37° C., was added: 16 µl 5×Sequenase ® buffer+8 µl 1 µM 288EOL1. The resulting mixture was spun briefly to collect the fluid into a single volume, and DNAs were allowed to anneal at room temperature for 15 min then 5.5 µl of the following mixture was added to each tube:

| x1 | x8 | | |
|---|---|---|---|
| 1 | 8 | 1 M | DTT |
| 0.4 | 3.2 | undiluted | labelling mix |
| 0.5 | 4 | | $[a^{35}S]dATP$ |
| 0.25 | 2 | undiluted | Sequenase TM |
| 3.35 | 27 | | water |

Reactions were thus labelled for 5 minutes at room temperature when 3.5 µl of each reaction was distributed into tubes containing 2.5 µl termination solutions G, A, T, and C.

After 5 to 6 minutes at room temperature, 4 µl of reaction stop solution was added to each tube, then the tubes were frozen −20°.

Sequences for maize loci 288 and 451, for various maize cultivars, are presented at FIGS. 13 and 14.

We claim:

1. A method for detecting variations in nucleic acid sequences, comprising
   (A) synthesizing a first primer which is complementary to a nonpolymorphic region of a genome of a test organism;
   (B) synthesizing at least a second primer and a third primer, each of said second and third primers directly and detectably distinguishing between different sequence variations of a first polymorphic region of said genome, wherein said second and said third primers do not hybridize to the same DNA strand of said genome as said first primer;
   (C) labelling said second and third primers, respectively, with chromophores that are distinguishable, one from the other, in terms of fluorescent spectrum;
   (D) contacting all of said first, second and third primers with genomic DNA from said test organism under stringent hybridizing conditions, thereby to produce hybridization products;
   (E) amplifying said hybridization products, wherein said amplifying is accomplished by polymerase chain reaction to produce amplification products; and then
   (F) analyzing fluorescent spectra of said amplification products to determine which labels and by inference, which variations in said first polymorphic region of said genome are present.

2. A method of claim 1 wherein said test organism is a eukaryote.

3. A method of claim 1, wherein said test organism is a plant.

4. A method of claim 1, wherein said all primers are at least sixteen nucleotides in length.

5. A method of claim 1, wherein said polymerase chain reaction is accomplished with Taq polymerase.

6. A method of claim 1, wherein said polymerase chain reaction is accomplished with Sequenase ®, a modified T7 DNA polymerase.

7. A method of claim 1, wherein said fluorescent spectra are generated by light excitation of the chromores via a laser beam.

8. A method of claim 7, wherein said laser beam is a broad-band laser beam.

9. The method of claim 1, wherein the first polymorphic region further comprises a plurality of polymorphic regions, and each of at least the second and the third primers distinguish between different sequence variations of each of said polymorphic regions.

* * * * *

UNITED STATES PATENT AND TRADEMARK OFFICE
CERTIFICATE OF CORRECTION

PATENT NO. : 5.324.631
DATED : June 28. 1994
INVENTOR(S) : Helentjaris et al.

It is certified that error appears in the above-indentified patent and that said Letters Patent is hereby corrected as shown below:

On title page, Item [76], under Inventors, please add --S. Mark Lee, 6405 Kilheggan Way, Elk Grove, California 95758--;
Item [73], under Assignee, please add --Pioneer Hi-Bred International, Inc., Des Moines, Iowa--.

Signed and Sealed this

Twentieth Day of December, 1994

Attest:

BRUCE LEHMAN

Attesting Officer     Commissioner of Patents and Trademarks